United States Patent
Alcaraz et al.

(10) Patent No.: US 7,047,661 B2
(45) Date of Patent: May 23, 2006

(54) SOLID PHASE MICROEXTRACTION FIBER CLEANING AND CONDITIONING APPARATUS AND METHOD

(75) Inventors: Armando Alcaraz, Livermore, CA (US); Michael H. Wiefel, Castro Valley, CA (US)

(73) Assignee: The Regents of the University of California, Oakland, CA (US)

( * ) Notice: Subject to any disclaimer, the term of this patent is extended or adjusted under 35 U.S.C. 154(b) by 223 days.

(21) Appl. No.: 10/421,582

(22) Filed: Apr. 22, 2003

(65) Prior Publication Data

US 2004/0025302 A1 Feb. 12, 2004

Related U.S. Application Data

(60) Provisional application No. 60/375,119, filed on Apr. 22, 2002.

(51) Int. Cl.
*F26B 25/04* (2006.01)

(52) U.S. Cl. .............................. 34/218; 34/219; 34/234; 34/241; 34/443

(58) Field of Classification Search .................. 34/443, 34/516, 218, 219, 227, 234, 241; 19/200; 436/178, 180, 181; 15/256.6; 8/137, 137.5
See application file for complete search history.

(56) References Cited

U.S. PATENT DOCUMENTS 5,691,206 A 11/1997 Pawliszyn 6,537,827 B1 * 3/2003 Pawliszyn ................... 436/178
6,623,545 B1 * 9/2003 Thordarson et al. ........... 95/45
2002/0182746 A1 * 12/2002 Mester et al. ............... 436/178

OTHER PUBLICATIONS

Koziel, Jacek A. et al, Fiber Conditioners for Solid Phase Microextraction: Design, Testing and Application, Short Communications.

* cited by examiner

*Primary Examiner*—Jiping Lu
(74) *Attorney, Agent, or Firm*—James S. Tak; Alan H. Thompson

(57) ABSTRACT

A SPME-fiber cleaning and conditioning apparatus and method having an elongated heating chamber with first and second opposite ends. The first end is capable of insertably receiving a SPME fiber portion of a SPME device, and the second end is a fluid outlet. A heater is provided for heating the chamber and heat-treating an inserted SPME fiber. Contaminants and other particles are agitated, desorbed and purged from the inserted SPME fiber by flowing a fluid through the chamber from the first end to the second end, away from the SPME device. Additionally, turbulence may be produced in the flow at a location adjacent the first end, to enhance agitation, desorption, and purging. A holder may also be provided extending from the first end for supporting the SPME device in a substantially horizontal orientation when the SPME fiber is positioned in the chamber.

26 Claims, 3 Drawing Sheets

SOLID PHASE MICROEXTRACTION FIBER CLEANING AND CONDITIONING APPARATUS AND METHOD

I. CLAIM IN PROVISIONAL APPLICATION

This application claims the benefit of U.S. Provisional Application No. 60/375,119 filed Apr. 22, 2002, entitled "Solid Phase Microextraction Fiber Cleaner/conditioning Unit" by Armando Alcaraz and Michael H. Wiefel.

The U.S. Government has rights in this invention pursuant to Contract No. W-7405-ENG-48 between the U.S. Department of Energy and the University of California for the operation of Lawrence Livermore National Laboratory.

II. FIELD OF THE INVENTION

The present invention relates to fiber cleaning and conditioning, and more particularly to an apparatus and method for cleaning and conditioning solid phase microextraction (SPME) fibers without using a gas chromatograph.

III. BACKGROUND OF THE INVENTION

Field characterization of suspect toxic chemicals requires the collection, isolation, and concentration of trace amounts of residues in, for example, air, soil, and liquid samples. Solid phase microextraction (SPME) is one known method developed for such a purpose using commercially-available, syringe-like SPME sample collection devices employing a variety of coated SPME fibers. The coated SPME fiber is typically housed in the needle (used for piercing a septum) of a GC-MS syringe, and can be mechanically extended and thus exposed to both collect analytes from the environment or sample fluid, and desorb analytes such as in an injection pod of a standard gas chromatograph (GC). SPME is a chemical sampling technique which adsorbs/absorbs analytes from the sample without the use of solvents or the need for exhaustive extractions. SPME presents many advantages over traditional analytical methods by combining sampling, pre-concentration, and transfer of analytes into a standard gas chromatograph (GC) for analysis.

A problem often seen in practice, however, is the use of GC injection ports to clean and condition SPME fibers. This practice poses a risk of carryover/cross contamination of non-target analytes between samplings. In addition, valuable analyst and instrumental analysis time may be wasted using a GC to clean and condition SPME fibers. Initial conditioning is typically required for new SPME fibers for time periods ranging from 0.5 to 4 hours at manufacturer-recommended temperatures ranging from 210 C. to 320 C. Additional cleaning time is also required to prepare ultra-clean SPME fibers for GC applications, such as field sampling, in order to reduce desorption time in a GC injector and ensure against carryover of contaminants or interfering chemical background.

One type of fiber conditioner addressing the aforementioned problem of GC injector usage for cleaning and conditioning, is disclosed in the article "*Fiber Conditions for Solid Phase Microextraction: Design, Testing, and Application*" by Koziel et al (J. High Resol. Chromatogr., 2000) As shown in FIG. 1 of the article, the fiber conditioner includes a stainless steel tube with a ceramic heating element for a heat source. The SPME fiber is inserted into an enlarged opening and positioned adjacent the heating element. Additionally, hot gas is flowed from an opposite end of the enlarged opening and directed toward the SPME fiber, and ultimately expelled through the enlarged opening. For fiber cleaning applications intended for fiber re-use, this arrangement may cause contamination of user-handled portions of a SPME device due to the expulsion of contaminants toward the SPME device, posing a potential safety risk for the analyst as well as risking cross-contamination for subsequent samplings.

There is therefore a need for an alternative SPME fiber cleaning and conditioning method and apparatus which provides safe, efficient, and effective SPME fiber cleaning and conditioning while minimizing the risk of contamination on the SPME device.

IV. SUMMARY OF THE INVENTION

One aspect of the present invention includes a SPME fiber cleaning and conditioning apparatus comprising: an elongated chamber having a first end capable of receiving therethrough a SPME fiber of a SPME device, and a second opposite end having a fluid outlet; a heater for heating the chamber and heat-treating the SPME fiber; and means for flowing a fluid through the chamber from the first end to the second end to agitate, desorb and purge the SPME fiber of contaminants in a direction away from the SPME device.

Another aspect of the present invention includes a SPME fiber cleaning and conditioning apparatus comprising: an elongated chamber for receiving therein a SPME fiber of a SPME device; a heater for heating the chamber and heat-treating the SPME fiber; and means for turbulently flowing a fluid through the chamber around the SPME fiber to enhance agitation, desorption, and purging of contaminants therefrom.

Another aspect of the present invention includes a method of cleaning and conditioning SPME fibers comprising the steps of: inserting a SPME fiber of a SPME device into an elongated chamber through a first end thereof, said elongated chamber having first and second opposing ends; heating the chamber to heat-treat the SPME fiber; and flowing a fluid through the chamber from the first end to the second end to agitate, desorb and purge the SPME fiber of contaminants in a direction away from the SPME device.

And another aspect of the present invention includes a method of cleaning and conditioning SPME fibers comprising the steps of: positioning a SPME fiber of a SPME device in an elongated chamber; heating the chamber to heat-treat the SPME fiber; and turbulently flowing a fluid through the chamber around the SPME fiber to enhance agitation, desorption, and purging of contaminants therefrom.

V. BRIEF DESCRIPTION OF THE DRAWINGS

The accompanying drawings, which are incorporated into and form a part of the disclosure, are as follows.

VI. DETAILED DESCRIPTION

The present invention is a SPME fiber cleaner and conditioner which operates to heat-treat and bake a SPME fiber, and uses an adjustable inert gas, such as nitrogen, to purge contaminates from the SPME fiber. In this manner, the unit serves to clean and condition SPME fibers of SPME sample collection devices (SPME device) used in the collection, isolation, and concentration of trace amounts of, for example, high explosives, chemical weapons, biological warfare related materials, and other residues in air, soil, vegetation, and liquid samples, among others. The SPME fiber cleaner and conditioner is operable as a standalone unit apart from a gas chromatograph (GC), to free up the GC to perform analytical work. Additionally, the SPME fiber cleaner and conditioner may be used to clean/condition out in the field as a battery operated, self-contained system, or in the laboratory in conjunction with other test equipment. While the term "SPME fiber cleaner and conditioner" is utilized herein and in the claims, it is appreciated that the present invention may be utilized to clean, condition, or clean and condition SPME fibers, as required by the application.

Figure 1:
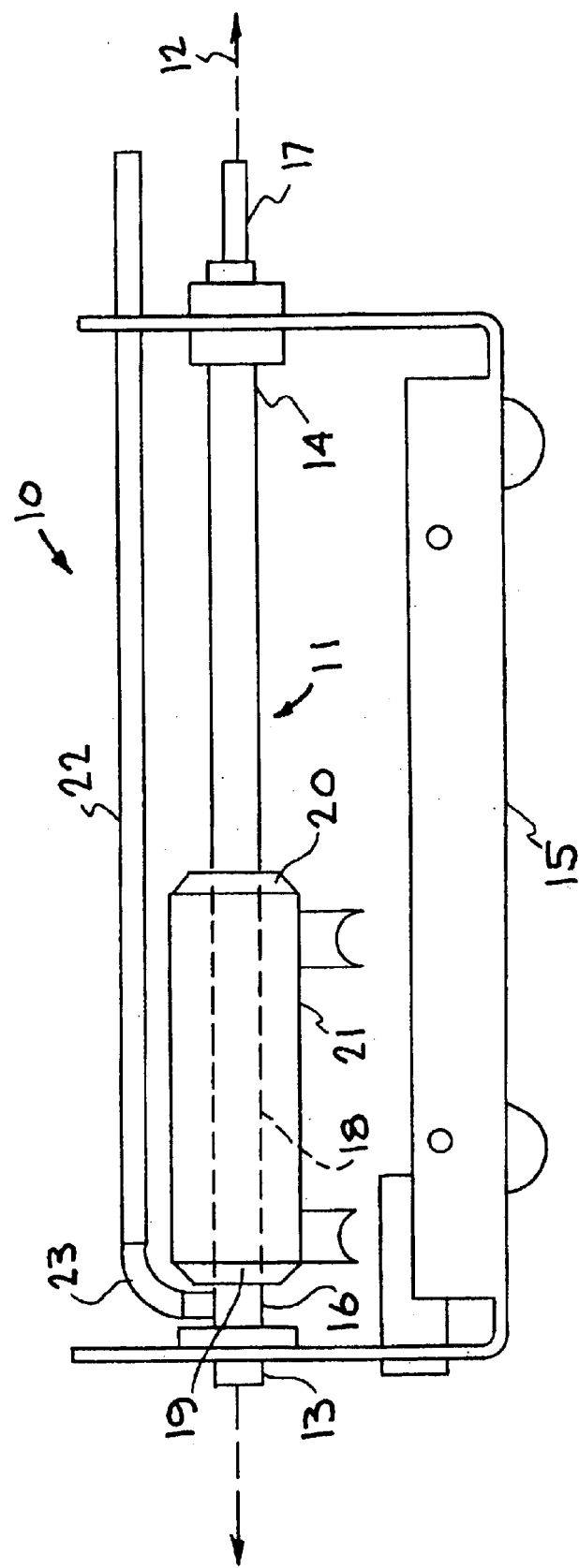
FIG. 1 is a schematic side view of an exemplary elongated heating chamber and flow channel of the SPME fiber cleaning and conditioning apparatus of the present invention, which perform the heating and purging functions.
Figure 2:
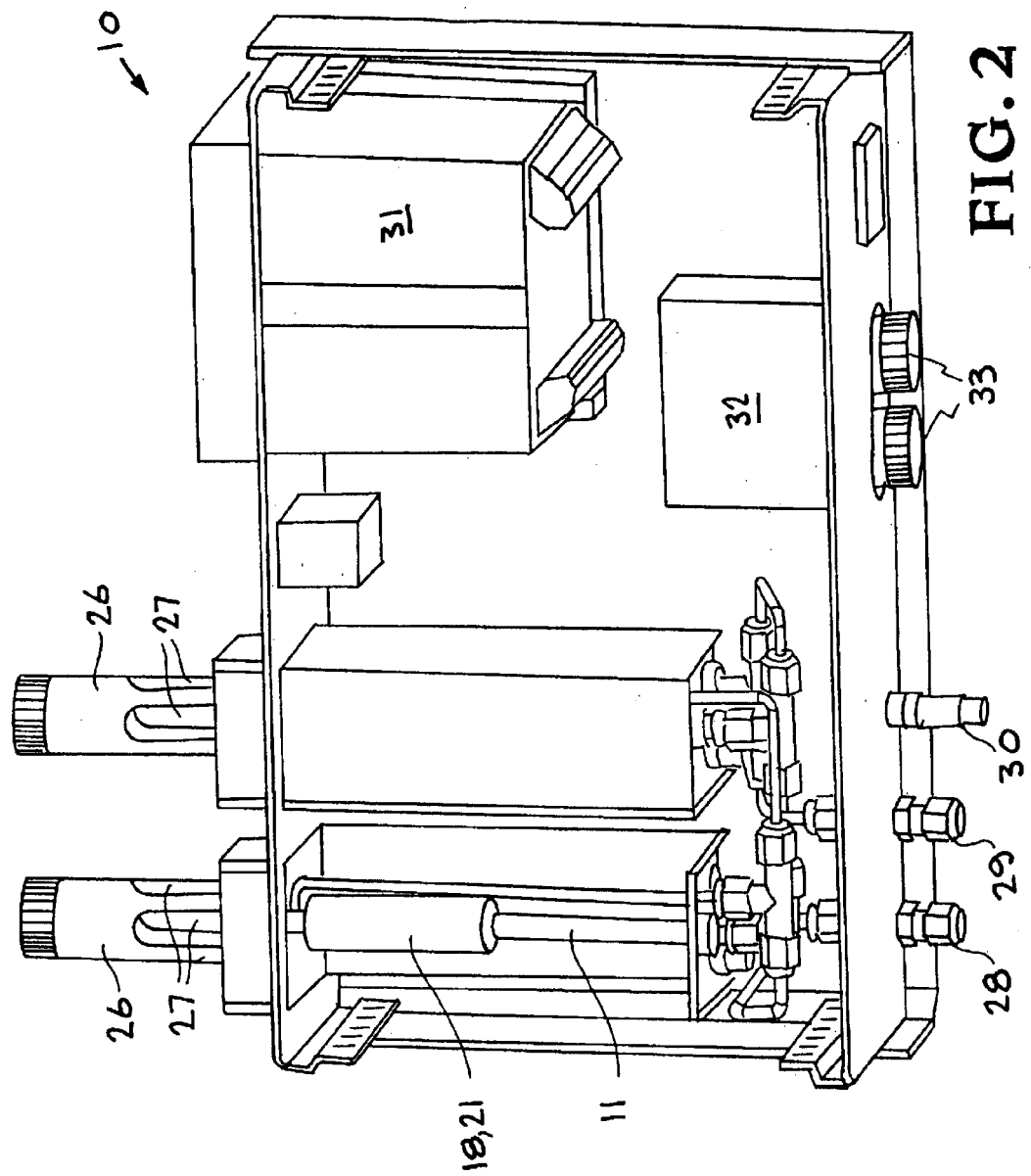
FIG. 2 is a top perspective view of an exemplary construction of the SPME fiber cleaning and conditioning unit of the present invention.
Figure 3:
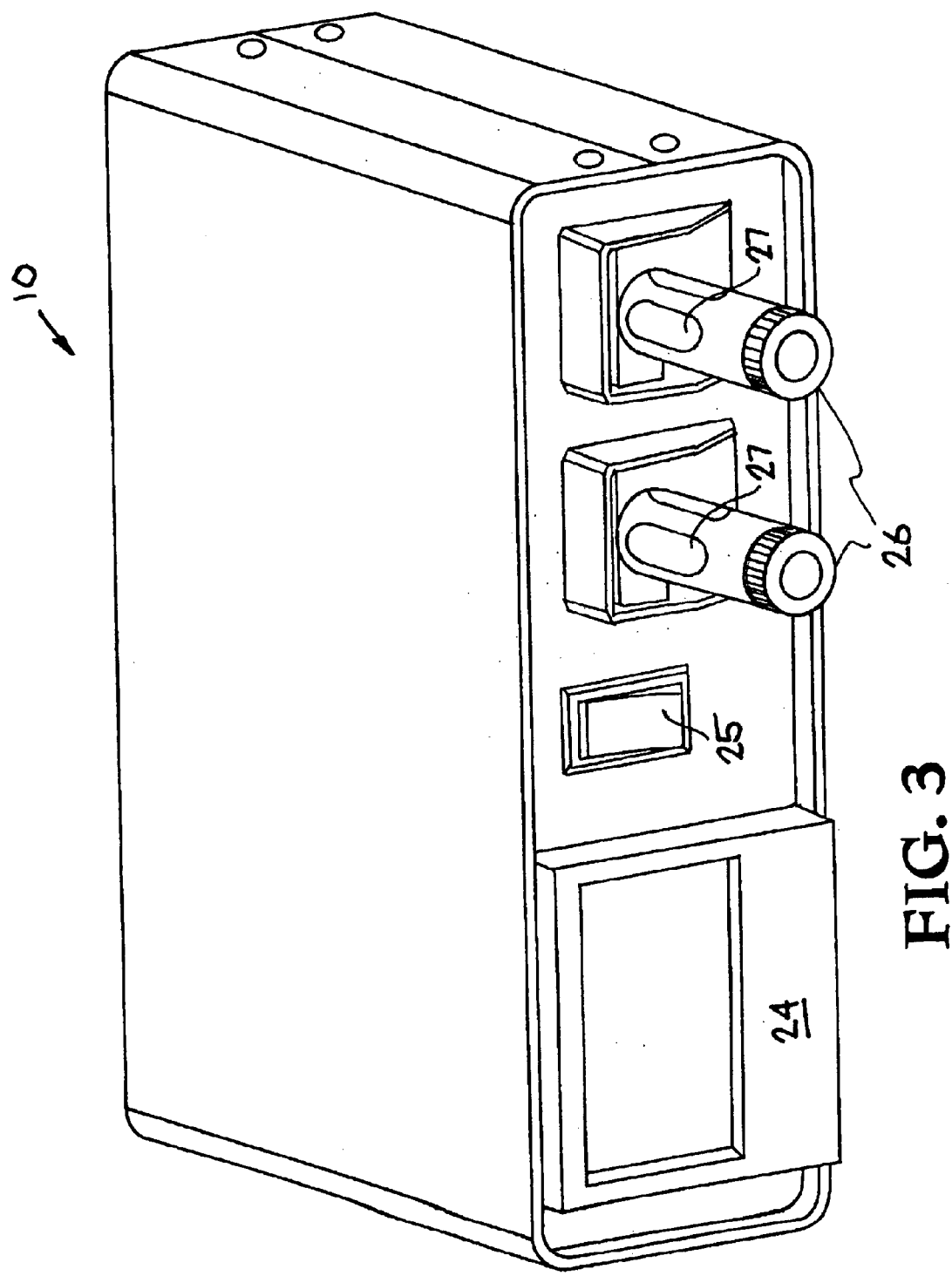
FIG. 3 is a front perspective view of the exemplary construction of FIG. 2.

Turning now to the figures, FIGS. 1–3 show an exemplary embodiment of the SPME fiber cleaner and conditioner ("cleaner") of the present invention, generally indicated at reference character 10. FIG. 1 in particular shows a schematic side view of an exemplary arrangement of the functional components of the cleaner 10 which perform the heating and purging steps. A mounting structure 15 is shown having a rigid construction on which the functional components are secured. And an elongated fluid conduit, such as flow tube 11 having an upstream end 13 and a downstream end 14 and defining a centerline 12, is secured to front and rear vertical sections of the structure 15. The elongated tube 11 preferably has a rigid thermally-conductive construction, such as stainless steel. And, while not shown, the upstream end 13 is an open end having a pierceable septum, whereby a needle or other piercing portion of a SPME device may be used to pierce the septum and a SPME fiber extended therethrough.

As can be further seen in FIG. 1, an elongated section 18 of the tube 11 near the upstream end 13 is provided with a heater element, such as a resistive heater coil or pad 21 surrounding the elongated section, for heating the elongated section. While the elongated section is shown as a continuous section of the flow tube 11, it is characterized as a chamber (hereinafter "elongated chamber") where heating takes place, and extending from a first end 19 to a second opposite end 20. The length of the chamber 18 may be suitably chosen to span the length of an inserted SPME fiber when fully extended through the upstream end 13 and through the septum and first end 19 of the chamber. The heater 21 is preferably of a type variably controllable for a range of baking temperatures, such as from 200 C. to over 300 C. Furthermore, a timer (not shown) may be incorporated for heating the chamber for user-specified durations.

FIG. 1 also shows a fluid line 22 connecting a fluid source (not shown) to a segment 16 of the flow tube 11 leading into the first end 19 of the elongated chamber 18, to provide for the desorption and subsequent purging of fiber contaminants and enable fast SPME fiber cleaning and conditioning. As characterized by the upstream and downstream designations of the ends 13 and 14 of the flow tube 11, the direction of a fluid flow, such as flowing gas, through the elongated chamber 13 is likewise from the first end 19 to the second end 20 of the chamber 18, where the second end 20 is a fluid outlet leading out of the chamber. As can be seen, the fluid outlet is opposite the first end 19 which receives the SPME fiber, and thus the stripping fluid used for purging is directed away from the SPME device, together with any contaminants. The flow direction away from the SPME device enables the exhaust fluid to be optionally collected, or filtered or otherwise processed prior to release into the atmosphere, without interfering or otherwise adversely affecting the inserted SPME device.

Additionally, the fluid line 22 in FIG. 1 is shown connected to the flow tube 11 by means of a connector end 23 substantially normal to the centerline 12 of the flow tube 11. This exemplary manner of connection serves the purpose of abruptly redirecting the fluid flow into the chamber 18 and inducing turbulence and turbulent flow through the chamber 18. Consequently, the induced turbulence increases diffusion and vorticity at or around the SPME fiber at the location of the SPME fiber to provide greater desorption of contaminants from the fiber. It is appreciated that alternative methods of inducing turbulence may also be provided at and around the SPME fiber, such as by providing an impediment or partial obstruction in an upstream location of the flow, or by actively producing turbulence at the SPME fiber or prior to entry into the elongated chamber. In any case, inducing turbulence enhances agitation, desorption, and purging of contaminants from the SPME fiber by creating irregular eddying motions that are very effective in promoting transport and diffusion of momentum, heat, and matter from one part of the flow to another.

FIGS. 2 and 3 show an illustrative construction of the SPME cleaning and conditioning unit 10 of the present invention, having a pair of heating chambers for cleaning/conditioning two SPME fibers (not shown) simultaneously and independently. The unit may be constructed using and modifying commercially available parts and equipment, such as a Hamilton syringe cleaner manufactured by Supelco of Bellefonte, Pennsylvania. As shown in FIG. 2, a platform/frame 34 provides the base for mounting the various operational components of the cleaner 10. A controller box 31 is shown mounted in the frame 34 generally including control, timer, and/or power management electronics (not shown), power supply (not shown), etc, necessary for controlling and operating the unit. And the control electronics preferably includes a digital variable temperature controller. And in FIG. 3, a front view of the unit is shown, having a power switch 25 and a display 24 where the various control and timer functions may be viewed.

Additionally, FIGS. 2 and 3 show the use of horizontally-oriented SPME device holders 26 associated with a corresponding elongated chamber 18, for supporting a SPME device while the SPME fiber is positioned within the elongated chamber to prevent SPME fiber damage or breakage. The holders are shown as rigid support arms having a tubular configuration and at least one slot which enables viewing of a septum at or near the first end, to ensure proper alignment into the chamber when piercing through the septum with a needle portion of the SPME device. The holders are constructed from a rigid material such as metal or metal alloy, or rigid polymer. Preferably, the holders are also constructed from a low thermal conductive material, such as the polymer having the trademark Delrin, to minimize heat transfer to the SPME device held by the holders. In FIG. 2, a storage component 32 is also provided for storing the holders/support arms during transport, or storing additional SPME device holders.

While particular operational sequences, materials, temperatures, parameters, and particular embodiments have been described and or illustrated, such are not intended to be limiting. Modifications and changes may become apparent to those skilled in the art, and it is intended that the invention be limited only by the scope of the appended claims.

What is claimed is:

1. A standalone SPME fiber cleaning and conditioning apparatus comprising:

an elongated chamber having a first end capable of receiving therethrough a SPME fiber of a SPME device, and a second opposite end having a fluid outlet leading out to the atmosphere;

a heater for heating the chamber and heat-treating the SPME fiber; and means for flowing a fluid through the chamber from the first end to the second end and out to the atmosphere, to agitate, desorb and purge the SPME fiber of contaminants in a direction away from the SPME device.

2. The apparatus as in claim 1, wherein the means for flowing induces turbulence at the SPME fiber to enhance agitation, desorption, andpurging of contaminants therefrom.

3. The apparatus of claim 2, wherein the means for flowing induces turbulence at the SPME fiber by flowing the fluid to a location adjacent the first end and abruptly redirecting the fluid flow into the chamber through the first end.

4. The apparatus as in claim 1, further comprising means for holding the SPME device in a substantially horizontal orientation adjacent the first end while the SPME fiber is received in the chamber.

5. The apparatus as in claim 4, wherein the holding means includes a support arm extending from the first end to substantially support the SPME device while the SPME fiber is received in the chamber.

6. The apparatus as in claim 5, wherein the support arm has a tubular configuration.

7. The apparatus as in claim 5, wherein the support arm has at least one slot which enables viewing of a septum at the first end and ensure alignment when piercing therethrough with a needle portion of the SPME device.

8. The apparatus as in claim 1, wherein nitrogen gas is used for the fluid flow.

9. A standalone SPME fiber cleaning and conditioning apparatus comprising:

an elongated chamber for receiving therein a SPME fiber of a SPME device;

a heater for heating the chamber and heat-treating the SPME fiber; and means for turbulently flowing a fluid through the chamber around the SPME fiber and out to the atmosphere, to enhance agitation, desorption, and purging of contaminants therefrom.

10. The apparatus as in claim 9, wherein the chamber has a first end capable of receiving the SPME fiber therethrough and a second opposite end having a fluid outlet leading out to the atmosphere and the turbulent flow through the chamber is from the first end to the second end in a direction away from the SPME device.

11. The apparatus as in claim 10, wherein the means for turbulently flowing induces turbulence at the SPME fiber by flowing the fluid to a location adjacent the first end and abruptly redirecting the fluid flow into the chamber through the first end.

12. The apparatus as in claim 9, further comprising means for holding the SPME device in a substantially horizontal orientation adjacent the first end while the SPME fiber is received in the chamber.

13. The apparatus as in claim 12, wherein the holding means includes a support arm extending from the first end to substantially support the SPME device while the SPME fiber is received in the chamber.

14. The apparatus as in claim 13, wherein the support arm has a tubular configuration.

15. The apparatus as in claim 13, wherein the support arm has at least one slot which enables viewing of a septum at the first end when piercing therethrough with a needle portion of the SPME device.

16. The apparatus as in claim 9, wherein nitrogen gas is used for the fluid flow.

17. A standalone method of cleaning and conditioning SPME fibers comprising the steps of:

inserting a SPME fiber of a SPME device into an elongated chamber through a first end thereof, said elongated chamber having a second end opposite the first end leading out to the atmosphere;

heating the chamber to heat-treat the SPME fiber; and flowing a fluid through the chamber from the first end to the second end and out to the atmospheres to agitate, desorb and purge the SPME fiber of contaminants in a direction away from the SPME device.

18. The method of claim 17, wherein the fluid is turbulently flowed through the chamber around the SPMIE fiber to enhance agitation, desorption, and purging of contaminants therefrom.

19. The method of claim 18, wherein the turbulent flow is induced at the SPME fiber by flowing the fluid to a location adjacent the first end and abruptly redirecting the fluid flow into the chamber through the first end.

20. A standalone method of cleaning and conditioning SPME fibers comprising the steps of:

positioning a SPME fiber of a SPME device in an elongated chamber;

heating the chamber to heat-treat the SPME fiber; and turbulently flowing a fluid through the chamber around the SPME fiber and out to the atmospheres to enhance agitation, desorption, and purging of contaminants therefrom.

21. The method as in claim 20, wherein the chamber has a first end capable of receiving the SPME fiber therethrough and a second opposite end having a fluid outlet leading out to the atmosphere and the turbulent flow through the chamber is from the first end to the second end in a direction away from the SPME device.

22. The method as in claim 21:

wherein the turbulent flow is induced at the SPME fiber by flowing the fluid to a location adjacent the first end and abruptly redirecting the fluid flow into the chamber through the first end.

23. A SPME fiber cleaning and conditioning apparatus comprising:

an elongated chamber having a first end capable of receiving therethrough a SPME fiber of a SPME device, and a second opposite end having a fluid outlet;

a heater for heating the chamber and heat-treating the SPME fiber; and means for flowing a fluid through the chamber from the first end to the second end to agitate, desorb and purge the SPME fiber of contaminants in a direction away from the SPME device, wherein the means for flowing induces turbulence at the SPME fiber to enhance agitation, desorption, and purging of contaminants therefrom by flowing the fluid to a location adjacent the first end and abruptly redirecting the fluid flow into the chamber through the first end.

24. A SPME fiber cleaning and conditioning apparatus comprising:
- an elongated chamber having a first end capable of receiving therethrough a SPME fiber of a SPME device, and a second opposite end having a fluid outlet;
- a heater for heating the chamber and heat-treating the SPME fiber;
- means for flowing a fluid through the chamber from the first end to the second end to agitate, desorb and purge the SPME fiber of contaminants in a direction away from the SPME device; and
- means for holding the SPME device in a substantially horizontal orientation adjacent the first end while the SPME fiber is received in the chamber, the holding means including a support arm extending from the first end to substantially support the SPME device while the SPME fiber is received in the chamber, and the support arm having at least one slot which enables viewing of a septum at the first end and ensure alignment when piercing therethrough with a needle portion of the SPME device.

25. A method of cleaning and conditioning SPME fibers comprising the steps of:
- inserting a SPME fiber of a SPME device into an elongated chamber through a first end thereof, said elongated chamber having first and second opposing ends;
- heating the chamber to heat-treat the SPME fiber; and
- flowing a fluid through the chamber from the first end to the second end to agitate, desorb and purge the SPME fiber of contaminants in a direction away from the SPME device, wherein the fluid is turbulently flowed through the chamber around the SPME fiber to enhance agitation, desorption, and purging of contaminants therefrom, and the turbulent flow is induced at the SPME fiber by flowing the fluid to a location adjacent the first end and abruptly redirecting the fluid flow into the chamber through the first end.

26. A method of cleaning and conditioning SPME fibers comprising the steps of:
- positioning a SPME fiber of a SPME device in an elongated chamber having a first end capable of receiving the SPME fiber therethrough and a second opposite end having a fluid outlet;
- heating the chamber to heat-treat the SPME fiber; and
- turbulently flowing a fluid through the chamber around the SPME fiber to enhance agitation, desorption, and purging of contaminants therefrom, wherein the turbulent flow through the chamber is from the first end to the second end in a direction away from the SPME device, and the turbulent flow is induced at the SPME fiber by flowing the fluid to a location adjacent the first end and abruptly redirecting the fluid flow into the chamber through the first end.

* * * * *